US00PP19441P2

(12) United States Plant Patent
Korlipara

(10) Patent No.: US PP19,441 P2
(45) Date of Patent: Nov. 11, 2008

(54) *ECHINACEA* PLANT NAMED 'PURITY'

(50) Latin Name: *Echinacea purpurea*
Varietal Denomination: Purity

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/986,272

(22) Filed: Nov. 19, 2007

(51) Int. Cl.
*A01H 5/00* (2006.01)

(52) U.S. Cl. ..... Plt./428

(58) Field of Classification Search ..... Plt./428
See application file for complete search history.

*Primary Examiner*—Annette H Para
*Assistant Examiner*—S. B. McCormick-Ewoldt
(74) *Attorney, Agent, or Firm*—Klarquist Sparkman, LLP

(57) ABSTRACT

A new and distinct *Echinacea* plant named 'Purity' characterized by medium-large, white flowers held above the foliage, large, orange cones on mature flowers, a medium-small, upright plant habit, well-branched upright flower stalks, and excellent vigor.

1 Drawing Sheet

Botanical denomination: *Echinacea purpurea.*
Variety designation: 'Purity'.

BACKGROUND OF THE INVENTION

The present invention relates to a new and distinct cultivar of *Echinacea* and given the cultivar name 'Purity'. *Echinacea* is in the family Asteraceae. This new cultivar originated as a third generation seedling from a planned breeding program using the *Echinacea purpurea* 'Fragrant Angel' (U.S. Plant Pat. No. 16,054) for the initial cross. The exact parents of this selection are unknown, unnamed proprietary, unreleased plants.

This new *Echinacea* cultivar is distinguished by:

1. medium-large, white flowers held above the foliage
2. large, orange cones on mature flowers
3. medium-small plant size
4. upright habit
5. well-branched upright flower stalks
6. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a one-year-old plant of *Echinacea* 'Purity' growing in the ground in full sun in the field in late summer in Canby, Oreg.

DETAILED PLANT DESCRIPTION

The following is a detailed description of the new *Echinacea* cultivar based on observations of a 9-month-old specimen growing in the ground in full sun in the trial fields under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—Grows to 45 cm wide and 62 cm tall to top of flowers.
- *Form.*—Basal clump.
- *Vigor.*—Excellent.
- *Roots.*—Fibrous, with many downward growing and few laterals, ivory in color (Yellow White 158D), roots develop easily from cuttings from the crown.

Stem (flowering):
- *Type.*—Ascending.
- *Size.*—Grows from 58 cm tall to terminal flower and 1.4 cm wide at base.
- *Internode length.*—2 cm to 11 cm.
- *Surface texture.*—Strigose.
- *Color.*—Yellow Green 146C.

Leaf (basal and stem):
- *Type.*—Simple.
- *Shape.*—Most lanceolate, upper stem leaves ovate.
- *Arrangement.*—Basal, stem leaves alternate.
- *Blade size.*—Grows to 18 cm long and 7.5 cm wide.
- *Margins.*—Coarsely serrate to entire.
- *Apex.*—Acuminate.
- *Base.*—Attenuate, continuing down petiole, clasping.
- *Surface texture.*—Strigose on both sides.
- *Venation.*—Pinnate.
- *Color.*—Topside, Yellow Green 147A with the vein Yellow Green 147B; bottom side Yellow Green 147A with the veins Yellow Green 147B.

*Petiole description.*—Grows to 15 cm long and 3 mm wide on basal leaves and 3 cm long and 7 mm wide on cauline leaves, strigose, Yellow Green 147B.

Inflorescence:

*Type.*—On long stalked terminal heads.

*Peduncle description.*—Grows from 59 cm tall from the base of the plant to the terminal flower and can grow to 11 cm long from the top leaf to the top of a flower head; diameter growing to 1 cm wide near the flower head; strigose, branched, with one to nineteen branches, 0 to 1 linear bract.

*Number of flowers per plant in first season.*—5 to 25, average 15.

*Number of peduncles per plant in first season.*—1 to 4, average 3.

*Bloom time.*—Summer until frost in Canby, Oreg.

*Immature inflorescence.*—4.3 cm wide and 3 cm deep, ray petals held upright and colored Green Yellow 1C, disc is Yellow Green 146B.

*Size.*—Grows to 11 cm wide and 7.5 cm deep as disc enlarges.

*Form.*—Ray petals held flat when young, older ray petals are a downward 10 degree angle, mature disc (or cone) is large and conic.

*Ray florets.*—22 to 28 per head, without pistil or stamen; oblanceolate with the tip two to three toothed and sometimes cupped up; margins entire, base attenuate, ray florets mostly overlapping; grows to 4.5 cm long, 15 mm wide; glabrous on both sides; topside White 155A with claw Yellow Green 144B, bottom side White 155A with tip Green Yellow 1C and claw Yellow Green 144B.

*Disc.*—Overall shape convex becoming conic; enlarges to 4.5 cm long and 5.5 cm wide; Orange 24B.

*Disc florets.*—About 200 in number, each 10 mm long, each with one persistent, very stiff bract with a spiny top which gives the disc color and a base which wraps around the disc floret; each bract 15 mm long, Orange 24B at the tip to Yellow Green 146B in the middle and White 155D at base; corolla 5 mm long and 1.5 mm wide, 5 lobed, Yellow Green 146B, glabrous; pistil 1 in number, 11 mm long, with an extruding, 2-branched stigma, spreading 2.5 mm wide, Yellow Green 145C, style 5 mm long, Yellow Green 154D, ovary 4 mm long and White 155A with Yellow Green 146B at top; stamen 5 mm long, anthers 3 mm long and Brown 200A, filaments 2 mm long, White 155D, pollen Yellow Orange 20B.

*Phyllaries.*—In 4 to 6 leafy series, area 4.8 cm wide and 1.5 cm deep, lobes ovate to lanceolate in shape, reflexed, can grow to 10 mm long and 5 mm wide, strigose and Yellow Green 147B on both sides, tip acute, entire.

*Bloom period.*—July through October in Canby, Oreg.

*Fragrance.*—Lovely.

Seed: Good fertility; average number of 24 seeds/head; each 7 mm long and 2.5 mm wide, oval, Greyed Green 196C.

Disease and pests: *Echinacea* are susceptible to leaf miners, powdery mildew, bacterial spots, and gray mold. None of these have been observed on plants grown under commercial conditions in Canby, Oreg. No resistance is known.

Comparisons to similar *Echinacea:* Compared to *Echinacea* 'Fragrant Angel' (U.S. Plant Pat. No. 16,054), one of the original parents in the breeding line, the new variety is much shorter and more compact.

Compared to *Echinacea* 'White Swan' (an unpatented plant), the new variety has larger flowers with the ray petals held more horizontally, orange rather than yellow cones, larger cones, and similar plant size.

I claim:

1. A new and distinct *Echinacea* plant as herein illustrated and described.

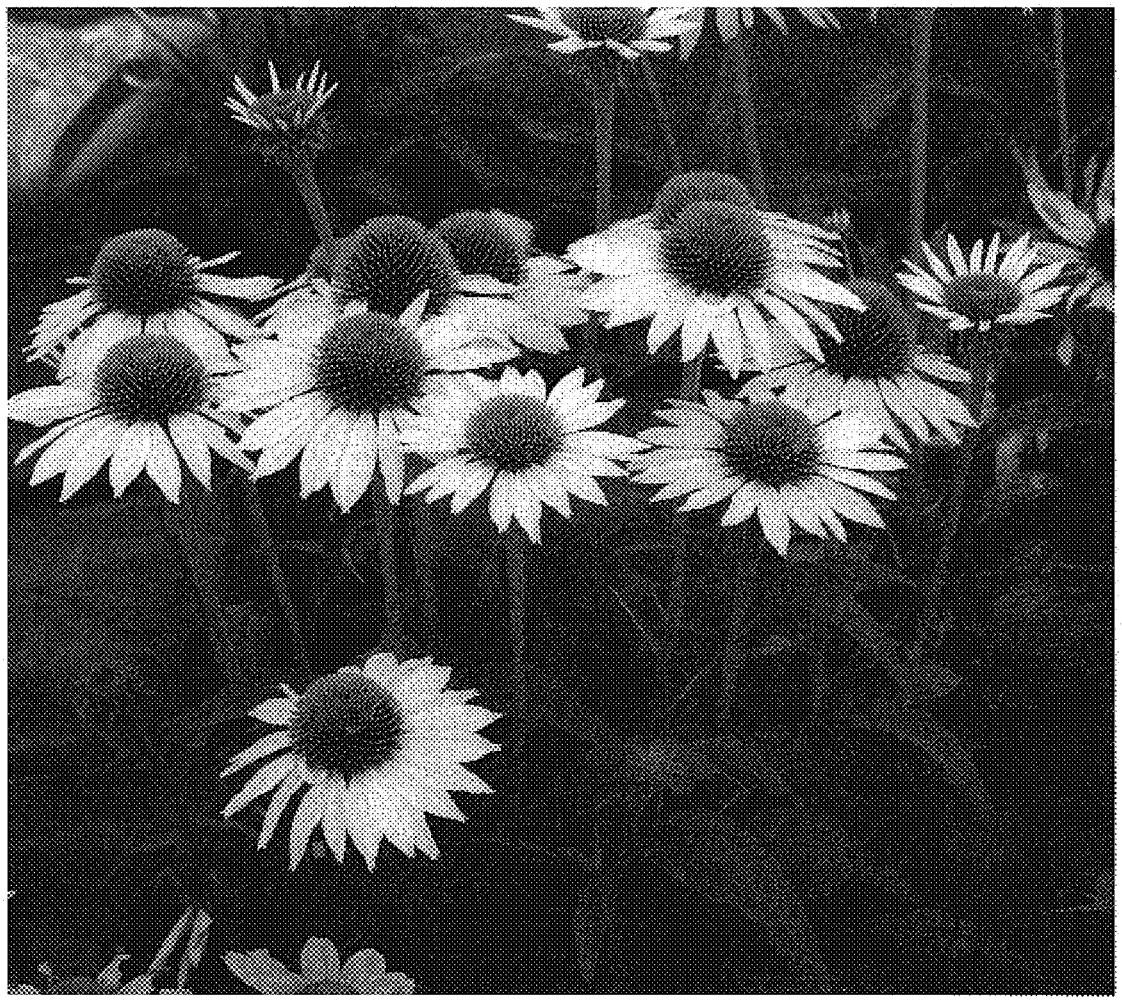

* * * * *